US006790641B2

(12) United States Patent  
Schauber et al.

(10) Patent No.: US 6,790,641 B2
(45) Date of Patent: Sep. 14, 2004

(54) LENTIVIRAL VECTOR PARTICLES RESISTANT TO COMPLEMENT INACTIVATION

(75) Inventors: Cherylene A. Schauber, San Francisco, CA (US); Christopher D. Pacheco, Ann Arbor, MI (US)

(73) Assignee: Cell Genesys, Inc., South San Francisco, CA (US)

( * ) Notice: Subject to any disclaimer, the term of this patent is extended or adjusted under 35 U.S.C. 154(b) by 0 days.

(21) Appl. No.: 10/425,323

(22) Filed: Apr. 29, 2003

(65) Prior Publication Data

US 2003/0207445 A1 Nov. 6, 2003

Related U.S. Application Data

(60) Provisional application No. 60/376,767, filed on May 1, 2002.

(51) Int. Cl.⁷ .......................... C12P 21/06; C12N 15/00; C12N 7/04
(52) U.S. Cl. .................... 435/69.1; 435/320.1; 435/236
(58) Field of Search .............................. 435/69.1, 320.1, 435/236, 5, 6, 69.7, 325; 536/23.72

(56) References Cited

U.S. PATENT DOCUMENTS

| | | |
|---|---|---|
| 5,665,577 A | 9/1997 | Sodroski et al. |
| 5,716,826 A | 2/1998 | Gruber et al. |
| 5,763,224 A | 6/1998 | Caras et al. |
| 6,013,516 A | 1/2000 | Verma et al. |

FOREIGN PATENT DOCUMENTS

| | | |
|---|---|---|
| WO | WO 99/27121 | 6/1999 |
| WO | WO 00/77233 A2 | 12/2000 |

OTHER PUBLICATIONS

Farson, D. et al., "A New–Generation Stable Inducible Packaging Cell Line for Lentiviral Vectors", *Human Gene Therapy*, May 20, 2001, vol. 12, pp. 981–997.

Kim, V. N., et al., "Minimal Requirement for a Lentivirus Vector Based on Human Immunodeficiency Virus Type 1", *Journal of Virology*, Jan. 1998, vol. 72, No. 1, pp. 811–816.

Saifuddin, M. et al., "Human immunodeficiency virus type 1 incorporates both glycosyl phosphatidylinositol–anchored CD55 and CD59 and integral membrane CD46 at levels that protect from complement–mediated destruction", *Journal of General Virology*, 1997, vol. 78, pp. 1907–1911.

Chang, et al., Efficacy and safety and analyses of a recombinant human immunodeficiency virus type 1 derived vector system, *Gene Therapy* (1999)6:715–728.

Farson et al., Large–Scale Manufacturing of Safe and Efficient Retrovirus Packaging Lines for Use in Immunotherapy Protocols, *The Journal of Gene Medicine* (1999) 1:195–209.

(List continued on next page.)

*Primary Examiner*—Hankyel T. Park
(74) *Attorney, Agent, or Firm*—Linda R. Judge; Gates & Cooper LLP

(57) ABSTRACT

The present invention provides a retroviral gene delivery system that resists complement inactivation through the incorporation of a complement regulatory protein into retroviral particles. In particular, the present invention provides a lentiviral packaging system comprising at least two vectors: a first vector which comprises a nucleotide sequence comprising a gag, a pol, or gag and pol genes; and a second vector which comprises a nucleotide sequence comprising a gene that encodes a complement regulatory protein (CRP) and, optionally, a gene that encodes a heterologous or functionally modified envelope protein. The genes encoding a heterologous or functionally modified envelope protein and a CRP are provided either together in a second nucleotide sequence, or separately in second and third nucleotide sequences. Producer cells comprising the packaging constructs of the present invention and a transgene can be used to produce recombinant retroviral particles for transgene delivery.

22 Claims, 3 Drawing Sheets

OTHER PUBLICATIONS

Gasmi, et al., Requirements for Efficient Production and Transduction of Human Immunodeficiency Virus Type 1–Based Vectors, *Journal of Virology*, Mar. 1999, pp. 1828–1834.

Huser, et al., Incorporation of decay–accelerating factor into the baculovirus envelope generates complement–resistant gene transfer vectors, *nature biotechnology*, vol. 19, May 2001, pp. 451–455.

Klages, et al., A Stable System for the High–Titer Production of Multiply Attenuated Lentiviral Vectors, *Molecular Therapy*, vol. 2, No. 2, Aug. 2000, pp. 170–176.

Klimatcheva, et al., Lentiviral Vectors and Gene Therapy, *Frontiers in Biosccience* Jun. 1, 1999; 4:D481–496.

Kumar et al., Large–Scale Production of Pseudotyped Lentiviral Vectors Using Baculovirus GP64, *Human Gene Therapy* (2003) 14:67–77.

Spitzer, et al., Complements–Protected Amphotropic Retroviruses from Murine Packaging Cells, *Human Gene Therapy* 10:1893–1902, Jul. 20, 1999.

Zufferey, et al., Multiply attenuated lentiviral vector achieves efficient gene delivery in vivo, *Nature Biotechnology*, vol. 15, Sep. 1997, pp. 871–875.

NCBI Accession No. M31516, Coding sequence for Human decay–acclerating factor, Nov. 2, 1994.

US 6,790,641 B2

LENTIVIRAL VECTOR PARTICLES RESISTANT TO COMPLEMENT INACTIVATION

This application claims priority to U.S. provisional application No. 60/376,767, filed May 1, 2002, the entire contents of which are incorporated herein by reference.

TECHNICAL FIELD OF THE INVENTION

The present invention relates to retroviral vectors and their use in gene therapy. In particular it relates to complement resistant lentiviral vectors. The invention provides novel lentiviral packaging vectors, stable packaging cell lines, stable producer cell lines, recombinant retroviruses carrying a foreign gene of interest and methods relating to the use thereof, as well as methods for producing recombinant lentivirus in mammalian cells.

BACKGROUND OF THE INVENTION

Retroviral vectors are a common tool for gene delivery (Miller, 1992, Nature 357: 455–460). The biology of retroviral proliferation enables such a use. Typically, wild type full length retroviral mRNAs serve both as a template for synthesis of viral proteins and as the viral genome. Such mRNAs encompass a region called the encapsidation signal which binds certain viral proteins thereby ensuring specific association of that mRNA with the produced virions. On infection of the target cell, reverse transcription of the retroviral mRNA into double stranded proviral DNA occurs. The retroviral enzyme, integrase, then binds to both long terminal repeats (LTR) which flank the proviral DNA and subsequently catalyzes the integration thereof into the genomic DNA of the target cell. Integrated proviral DNA serves as the template for generation of new full-length retroviral mRNAs.

Retroviral vectors have been tested and found to be suitable delivery vehicles for the stable introduction of a variety of genes of interest into the genomic DNA of a broad range of target cells. The ability of retroviral vectors to deliver unrearranged, single copy transgenes into a broad range of cells makes retroviral vectors well suited for transferring genes into cells. Unfortunately, in vivo use of retroviral gene delivery systems has been hindered by the inactivation of retroviruses by human serum. This inactivation may occur via complement-mediated lyses of retroviruses.

Attempts to protect gene transfer vectors from complement inactivation involve the co-administration of a soluble complement regulatory protein (CRP), or integration of a CRP into the viral membrane. One strategy has been used with murine leukemia virus, a retroviral delivery system, but requires the fusion of the catalytic domain of a CRP to a retroviral envelope protein in order to achieve incorporation of the CRP into viral particles (Spitzer et al., 1999, Human Gene Therapy 10:1893–1902). Another strategy has been the incorporation of a CRP into the baculovirus envelope to create a complement-resistant baculoviral vector for gene transfer (Hüser et al., 2001, Nature Biotechnology 19:451–455; WO 00/77233). This strategy also requires fusion of the CRP catalytic domain to the baculoviral envelope protein.

There remains a need for viral gene delivery systems that avoid immune responses directed against the transgene and resist complement inactivation without requiring the creation of a chimeric protein fusing CRP to a transmembrane region or the use of a separately administered product.

SUMMARY OF THE INVENTION

The invention disclosed herein offers a surprisingly feasible and efficient system for combining the advantages of retroviral gene delivery with complement resistance. The invention provides a lentiviral packaging system that comprises at least two vectors: a first vector comprises a first nucleotide sequence comprising a gag, a pol, or gag and pol genes; and a second vector comprises a second nucleotide sequence comprising a heterologous envelope gene and a gene that encodes a complement regulatory protein (CRP). In an alternative and preferred embodiment, the packaging system comprises at least three vectors, wherein the second nucleotide sequence comprises the envelope gene and not the CRP, and the gene encoding a CRP is provided on a third vector.

Preferably, the heterologous envelope gene comprises a VSV-G or baculoviral gp64 envelope gene. In a preferred embodiment, the lentivirus is HIV. A second or third generation packaging system is preferred, wherein the vectors lack a functional tat gene and/or functional accessory genes (vif, vpr, vpu, vpx, nef). In another preferred embodiment, the system further comprises an additional nucleotide sequence that comprises a rev gene. The packaging system can be provided in the form of a set of lentiviral vectors, or in the form of a packaging cell that contains the first, second, and, optionally, third nucleotide sequences. Preferably, the genes encoded by the nucleotide sequences are stably integrated into the genome of the packaging cell.

The invention further provides a producer cell that comprises the packaging system of the invention and a transgene. The producer cell of the invention is capable of producing a recombinant lentivirus that carries a transgene and resists complement inactivation. The recombinant lentivirus is capable of infecting a host cell, thereby delivering the transgene to the host cell for expression.

The invention additionally provides a method of delivering a transgene to a cell. The method comprises contacting the cell with a recombinant lentivirus of the invention. In one embodiment, the transgene is a therapeutic transgene. The cell can be in vivo, in vitro or ex vivo.

DETAILED DESCRIPTION OF THE INVENTION

Figure 1:
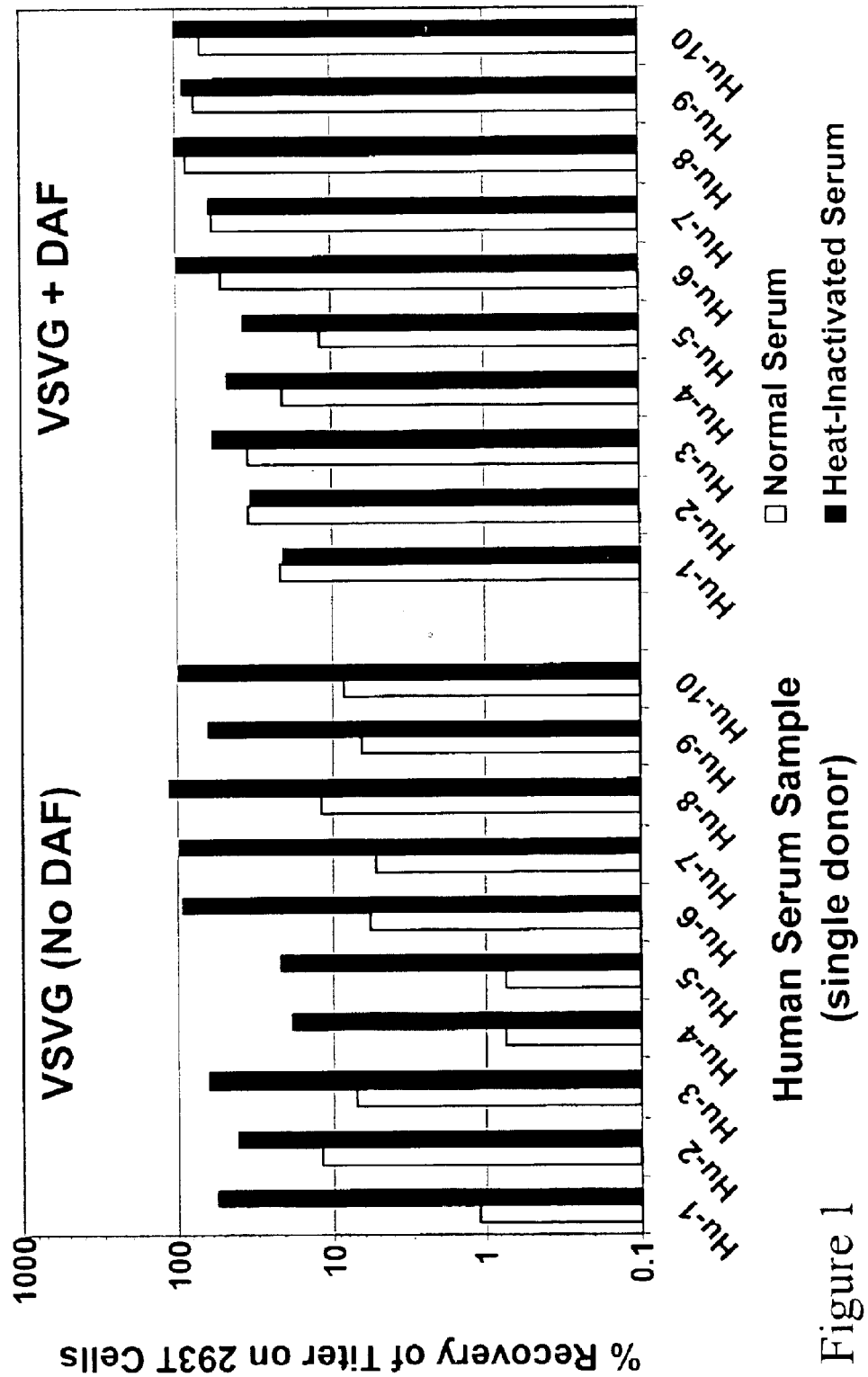
FIG. 1 is a bar graph showing that DAF/CD55 confers complement resistance to VSVG-Pseudotyped Lentiviral Vectors. Lentiviral vectors carrying the GFP transgene and pseudotyped with the VSV-G envelope glycoprotein were prepared by transient transfection and concentration by ultracentrifugation. One preparation (VSVG-No DAF, left) was made in the absence of any exogenous complement inhibitor protein and the other (VSVG+DAF, right) was generated by co-transfection of a mammalian expression plasmid encoding DAF/CD55. These vector preps were titered using 293T cells as targets. To determine complement sensitivity, serum samples from 10 single human donors were split in half and one half was heated at 56° C. for one hour to inactivate the complement activity. The vector samples were exposed to the normal (white bars) or heat-inactivated (black bars) serum from each donor for 1 hour at 37° C. and then titered on 293T cells. The resulting titer values are reported as a fraction of the titer recovered from a control sample that was not exposed to serum (100% recovery of titer).
Figure 2:
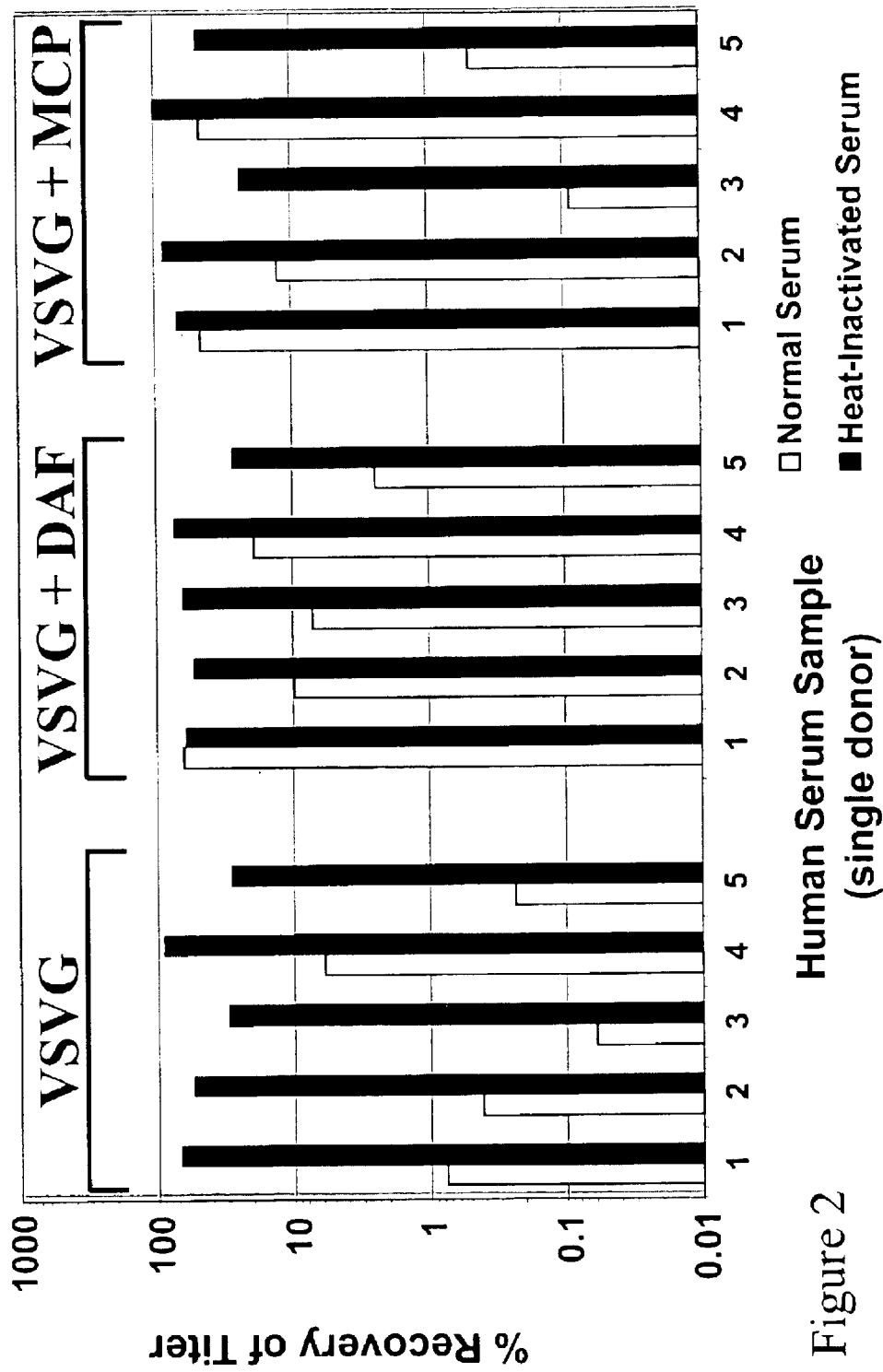
FIG. 2 is a bar graph showing that MCP/CD46 can also protect VSV-G pseudotyped lentiviral vectors from human complement inactivation. Lentiviral vectors with and without complement inhibitor proteins were tested for sensitivity to complement inactivation as in FIG. 1. The vector samples tested carried the GFP transgene and were pseudotyped with the VSV-G envelope glycoprotein. One preparation (VSVG, left) was made in absence of any exogenous complement inhibitor protein and the others (VSVG+DAF, middle) and (VSVG+MCP) were generated by co-transfection of mammalian expression plasmids encoding DAF/CD55 or MCP/CD46, respectively. The serum samples were from five single human donors.
Figure 3:
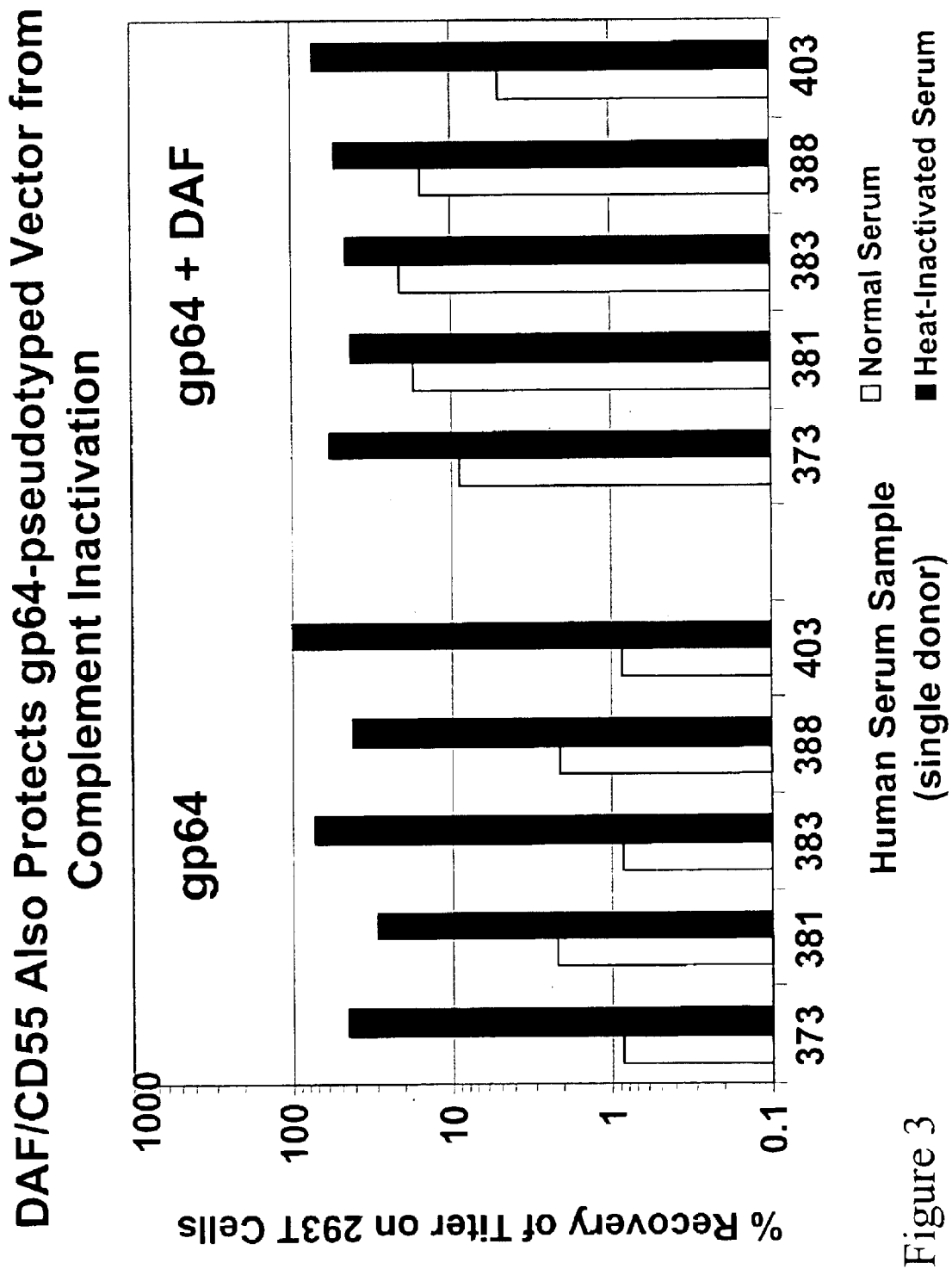
FIG. 3 is a bar graph showing that DAF/CD55 also protects gp64-pseudotyped vector from complement inactivation. Lentiviral vectors with and without complement inhibitor proteins were tested for sensitivity to complement inactivation as in FIG. 1. The vector samples tested carried the GFP transgene and were pseudotyped with the baculovirus gp64 envelope glycoprotein. One preparation (gp64, left) was made in absence of any exogenous complement inhibitor protein and the other (gp64+DAF, right) was generated by co-transfection of a mammalian expression plasmid encoding DAF/CD55. The serum samples were from five single human donors.

The invention is based on the discovery that CRPs are naturally incorporated into lentiviral particles and without requiring use of a chimeric molecule in which the CRP is fused to a transmembrane protein. Further, the resulting recombinant lentiviral particles have a demonstrated ability to resist complement inactivation upon exposure to serum. The invention thereby provides a gene therapy tool that offers enhanced efficiency and efficacy.

Definitions

All scientific and technical terms used in this application have meanings commonly used in the art unless otherwise specified. As used in this application, the following words or phrases have the meanings specified.

As used herein, "a" or "an" means at least one, unless clearly indicated otherwise.

As used herein, "nucleotide sequence", "nucleic acid sequence", "nucleic acid" or "polynucleotide" refers to a deoxyribonucleotide or ribonucleotide polymer in either single- or double-stranded form, and unless otherwise limited, encompasses known analogs of natural nucleotides that hybridize to nucleic acids in a manner similar to naturally-occurring nucleotides. Nucleic acid sequences can be, e.g., prokaryotic sequences, eukaryotic mRNA sequences, cDNA sequences from eukaryotic mRNA, genomic DNA sequences from eukaryotic DNA (e.g., mammalian DNA), and synthetic DNA or RNA sequences, but are not limited thereto.

As used herein, a "promoter" refers to a nucleic acid sequence capable of directing transcription.

As used herein, "expression control sequence" refers to a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed.

As used herein, a "retroviral transfer vector" refers to the expression vector that comprises a nucleotide sequence that encodes a transgene and that further comprises nucleotide sequences necessary for packaging of the vector. Preferably, the retroviral transfer vector also comprises the necessary sequences for expressing the transgene in cells.

As used herein, "vector particle", "retroviral particle", "viral particle", "retroviral vector particle" refers to a replication-defective retrovirus carrying an RNA transcribed from a retroviral vector of the present invention. Preferably, the RNA comprises a transgene sequence (transgene RNA) transcribed from a retroviral transfer vector of the present invention.

As used herein, "packaging system" refers to a set of viral constructs comprising genes that encode viral proteins involved in packaging a recombinant virus. Typically, the constructs of the packaging system will ultimately be incorporated into a packaging cell.

As used herein, a "second generation" lentiviral vector system refers to a lentiviral packaging system that lacks functional accessory genes, such as one from which the accessory genes, vif, vpr, vpu and nef, have been deleted or inactivated. See, e.g., Zufferey et al., 1997, Nat. Biotechnol. 15:871–875.

As used herein, a "third generation" lentiviral vector system refers to a lentiviral packaging system that has the characteristics of a second generation vector system, and that further lacks a functional tat gene, such as one from which the tat gene has been deleted or inactivated. Typically, the gene encoding rev is provided on a separate expression construct. See, e.g., Dull et al., 1998, J. Virol. 72(11): 8463–8471.

As used herein, "pseudotyped" refers to the replacement of a native envelope protein with a heterologous or functionally modified envelope protein.

As used herein, "heterologous" refers to that which is not endogenous to, or naturally occurring in, a referenced sequence, molecule (including e.g., a protein), cell, tissue, or organism. For example, a heterologous sequence of the present invention can be derived from a different species, or from the same species but substantially modified from an original form. Also for example, a nucleic acid sequence that is not normally expressed in a cell is a heterologous nucleic acid sequence.

As used herein, a "functionally modified" protein refers to a protein that has a different or altered activity or property of the protein from which the functionally modified protein was derived. Preferably, a heterologous or functionally modified envelope protein of the present invention has a different cellular or binding specificity as compared to the envelope protein from which the heterologous or functionally modified protein was derived. A functionally modified envelope protein of the present invention can be generated by modifying (e.g., by point mutation, deletion, fusion, or chemical coupling) an envelope protein from which it is derived. For example, a functionally modified envelope protein of the present invention may be an envelope protein that has a mutation and/or deletion, as compared to the envelope protein from which it was derived. Also, for example, a functionally modified envelope protein of the present invention may be an envelope protein that is fused or coupled to a ligand that binds to a specific cellular target (e.g., a receptor) and, thereby, the cellular and/or binding specificity of the envelope protein is altered, as compared to the envelope protein from which it was derived.

As used herein, a "gp64" gene refers to a baculoviral gp64 envelope gene. The sequence of a gp64 gene can be derived from the baculoviridae family. Representative gp64 genes and methods for preparing them are described in Monsma and Blissard, 1995, J. Virol. 69(4):2583–95; Blissard and Rohrmann, 1989, Virology 170(2):537–55; and Blissard and Monsma, U.S. Pat. Nos. 5,750,383 and 5,750,383. The gp64 or other baculoviral envelope gene can be from the baculoviridae family. For example, the gp64 or other baculoviral envelope gene can be from *Autographa californica* nucleopolyhedrovirus (AcMNPV), *Anagrapha falcifera* nuclear polyhedrosis virus, *Bombyx mori* nuclear polyhedrosis virus, *Choristoneura fumiferana* nucleopolyhedrovirus, *Orgyia pseudotsugata* single capsid nuclear polyhedrosis virus, *Epiphyas postvittana* nucleopolyhedrovirus, *Hyphantria cunea* nucleopolyhedrovirus, *Galleria mellonella* nuclear polyhedrosis virus, Dhori virus, Thogoto virus, *Antheraea pernyi* nucleopolyhedrovirus, or Batken virus. Preferably, the gp64 envelope gene is an AcMNPV gp64 envelope gene.

"Gene" as used herein refers to a nucleic acid sequence encoding at least one open reading frame that is capable of encoding a polypeptide or protein.

As used herein, "transgene" refers to a polynucleotide that can be expressed, via recombinant techniques, in a non-native environment or heterologous cell under appropriate conditions. The transgene may be derived from the same type of cell in which it is to be expressed, but introduced from an exogenous source, modified as compared to a corresponding native form and/or expressed from a non-native site, or it may be derived from a heterologous cell. "Transgene" is synonymous with "exogenous gene", "foreign gene" and "heterologous gene".

As used herein, a "therapeutic" gene refers to a gene that, when expressed, confers a beneficial effect on the cell or tissue in which it is present, or on a mammal in which the gene is expressed. Examples of beneficial effects include amelioration of a sign or symptom of a condition or disease, prevention or inhibition of a condition or disease, or conferral of a desired characteristic. Therapeutic genes include genes that correct a genetic deficiency in a cell or mammal.

As used herein, "subject" refers to the recipient of the therapy to be practiced according to the invention. The subject can be any animal, including a vertebrate, but will preferably be a mammal. If a mammal, the subject will preferably be a human, but may also be a domestic livestock, laboratory subject or pet animal.

As used herein, "significant toxicity" refers to a level of toxicity that contraindicates clinical use as determined by an art-accepted measure of toxicity. Examples of art-accepted measures of toxicity include, but are not limited to, elevated serum levels of an enzyme or other substance associated with liver toxicity, such as sGPT, creatinine, alkaline phosphatase and alanine aminotransferase (ALT). In one embodiment, elevated serum levels means higher than the upper limit of the normal range.

As used herein, "cytoxicity" refers to a level of toxicity that results in cell death, arrest in cell growth, or inactivation of cellular functions important for the viability of a cell.

As used herein, a "therapeutically acceptable amount" of a substance refers to a sufficient quantity of the substance that an amelioration of adverse symptoms or protection against adverse symptoms can be detected in a subject treated with the substance.

As used herein, "pharmaceutically acceptable carrier" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline or normal (0.9%) saline. Compositions comprising such carriers are formulated by well known conventional methods (see, for example, *Remington's Pharmaceutical Sciences,* 18th edition, A. Gennaro, ed., Mack Publishing Co., Easton, Pa., 1990).

Reference is made herein to techniques commonly known in the art. Guidance in the application of such techniques can be found, e.g., in Ausubel et al. eds., 1995, Current Protocols In Molecular Biology, and in Sambrook et al., 1989, Molecular Cloning: A Laboratory Manual, Cold Spring Harbor Laboratory Press, NY, the contents of which are incorporated herein by reference.

The patents and publications cited throughout the specification are incorporated herein by reference.

The present invention is not to be limited in scope by the embodiments disclosed herein, which are intended as single illustrations of individual aspects of the invention, and any that are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

Packaging Systems

The present invention provides retroviral packaging systems that comprises at least two vectors: a first packaging vector which comprises a nucleotide sequence comprising a gag, a pol, or gag and pol genes; and a second packaging vector which comprises a nucleotide sequence comprising a gene that encodes a CRP, and, optionally, a heterologous or functionally modified envelope gene. In a preferred embodiment, the gene encoding a CRP and the envelope gene are provided on separate constructs.

In preferred embodiments, the CRP is a decay-accelerating factor (DAF), also known as CD55, a glycosyl-phosphatidylinositol-anchored membrane protein that regulates complement activation on cell surfaces (Nicholson-Weller & Wang, 1994, J. Lab. Clin. Med. 123(4):485–91). DAF can be obtained from the American Type Culture Collection (Manassas, Va., USA), where an available human cDNA clone that expresses DAF is designated ATCC Accession No. 5530612. Other DAF molecules are known in the art, such as GenBank Accession No. M31516; see also Brodbeck et al., 1996, J. Immunol. 156:2528–2533.

Other CRPs include membrane cofactor protein (MCP; a classic transmembrane protein), complement receptor 1 (CR1), homologous restriction factor (HRF) and CD59. Like DAF, CD59 is anchored by a glycosyl-phosphatidylinositol anchor that is added in the endoplasmic reticulum. DAF, CR1 and MCP are thought to block the complement cascade by restricting the activity of the C3/C5 convertase enzyme, while CD59 and HRF are considered to act by inhibiting the formation of the membrane attack complex.

In another preferred embodiment, the retroviral elements are derived from a lentivirus, such as HIV. Preferably, the vectors lack a functional tat gene and/or functional accessory genes (vif, vpr, vpu, vpx, nef). In another preferred embodiment, the system further comprises a third packaging vector that comprises a nucleotide sequence comprising a rev gene. The packaging system can be provided in the form of a packaging cell that contains the first, second, and, optionally, third nucleotide sequences.

The invention is applicable to a variety of retroviral systems, and those skilled in the art will appreciate the common elements shared across differing groups of retroviruses. The description herein uses lentiviral systems as a representative example. However, all retroviruses share the features of enveloped virions with surface projections and containing one molecule of linear, positive-sense single stranded RNA, a genome consisting of a dimer, and the common proteins gag, pol and env.

Lentiviruses share several structural virion proteins in common, including the envelope glycoproteins SU (gp120) and TM (gp41), which are encoded by the env gene; CA (p24), MA (p17) and NC (p7–11), which are encoded by the gag gene; and RT, PR and IN encoded by the pol gene. HIV-1 and HIV-2 contain accessory and other proteins involved in regulation of synthesis and processing virus RNA and other replicative functions. The accessory proteins, encoded by the vif, vpr, vpu/vpx, and nef genes, can be omitted (or inactivated) from the recombinant system. In addition, tat and rev can be omitted or inactivated, e.g., by mutation or deletion.

First generation lentiviral vector packaging systems provide separate packaging constructs for gag/pol and env, and typically employ a heterologous or functionally modified envelope protein for safety reasons. In second generation lentiviral vector systems, the accessory genes, vif, vpr, vpu and nef, are deleted or inactivated. Third generation lentiviral vector systems are those from which the tat gene has been deleted or otherwise inactivated (e.g., via mutation).

Compensation for the regulation of transcription normally provided by tat can be provided by the use of a strong constitutive promoter, such as the human cytomegalovirus immediate early (HCMV-IE) enhancer/promoter. Other promoters/enhancers can be selected based on strength of constitutive promoter activity, specificity for target tissue (e.g., liver-specific promoter), or other factors relating to desired control over expression, as is understood in the art. For example, in some embodiments, it is desirable to employ an inducible promoter such as tet to achieve controlled expression. The gene encoding rev is preferably provided on a separate expression construct, such that a typical third generation lentiviral vector system will involve four plasmids: one each for gagpol, rev, envelope and the transfer vector. Regardless of the generation of packaging system employed, gag and pol can be provided on a single construct or on separate constructs.

The packaging vectors of the present invention comprise one or more genes encoding retroviral packaging elements, wherein each gene is operably linked to an expression control sequence. In one embodiment, the vector is a plasmid. In addition, other vectors suitable for use in the packaging systems of the present invention are known in the art and include, for example, viral vectors.

Typically, the packaging vectors are included in a packaging cell, and are introduced the cell via transfection, transduction or infection. Methods for transfection, transduction or infection are well known by those of skill in the art. A retroviral transfer vector of the present invention can be introduced into a packaging cell line, via transfection, transduction or infection, to generate a producer cell or cell line. Accordingly, the present invention further provides producer cells and cell lines that comprise the packaging system of the invention and a retroviral transfer vector. The producer cells or cell lines of the present invention are capable of producing a recombinant retrovirus that is pseudotyped with a heterologous or functionally modified envelope protein (e.g., a baculovirus envelope protein) and carries a transgene. The producer cells and cell lines can be cultured in media and the pseudotyped retrovirus recovered from the culture media and titrated using standard methods. Further, the pseudotyped retrovirus of the present invention is capable of infecting a host cell and, thereby, delivering the transgene to the host cell such that the transgene is expressed in the host cell.

The packaging vectors of the present invention can be introduced into human cells or cell lines by standard methods including, e.g., calcium phosphate transfection, lipofection or electroporation. In some embodiments, the packaging vectors are introduced into the cells together with a dominant selectable marker, such as neo, DHFR, Gln synthetase or ADA, followed by selection in the presence of the appropriate drug and isolation of clones. A selectable marker gene can be linked physically to genes encoding by the packaging vector.

Stable cell lines, wherein the packaging functions are configured to be expressed by a suitable packaging cell, are known. For example, see U.S. Pat. No. 5,686,279; and Ory et al., Proc. Natl. Acad. Sci. (1996) 93:11400–11406, which describe packaging cells. Further description of stable cell line production can be found in Dull et al., 1998, J. Virology 72(11):8463–8471; and in Zufferey et al., 1998, J. Virology 72(12):9873–9880

Zufferey et al., 1997, Nature Biotechnology 15:871–875, teach a lentiviral packaging plasmid wherein sequences 3' of pol including the HIV-1 envelope gene are deleted. The construct contains tat and rev sequences and the 3' LTR is replaced with poly A sequences. The 5' LTR and psi sequences are replaced by another promoter, such as one which is inducible. For example, a CMV promoter or derivative thereof can be used.

The packaging vectors of interest may contain additional changes to the packaging functions to enhance lentiviral protein expression and to enhance safety. For example, all of the HIV sequences upstream of gag can be removed. Also, sequences downstream of envelope can be removed. Moreover, steps can be taken to modify the vector to enhance the splicing and translation of the RNA.

Optionally, a conditional packaging system is used, such as that described by Dull et al., 1998, J. Virology 72(11):8463–8471. Also preferred is the use of a self-inactivating vector (SIN), which improves the biosafety of the vector by deletion of the HIV-1 long terminal repeat (LTR) as described, for example, by Zufferey et al., 1998, J. Virology 72(12):9873–9880. Inducible vectors can also be used, such as through a tet-inducible LTR.

Retroviral Vectors and Retroviruses

The present invention also provides methods of producing recombinant lentivirus. The methods comprise transforming a host cell with a packaging vector which comprises a first nucleotide sequence comprising a gag, a pol, or gag and pol genes; and a second packaging vector which comprises nucleotide sequence comprising a gene that encodes a CRP. Optionally, the second nucleotide sequence additionally includes a heterologous or functionally modified envelope gene. Alternatively, the envelope gene is provided on a separate packaging vector. Preferably, the CRP comprises DAF.

The retroviral vectors of the present invention, include e.g., retroviral transfer vectors comprising one or more transgene sequences and retroviral packaging vectors comprising one or more packaging elements. In some embodiments, the present invention provides pseudotyped retroviral vectors encoding a heterologous or functionally modified envelope protein for producing pseudotyped retrovirus.

The sequence of a heterologous or functionally modified envelope protein of the present invention can be derived from the sequence of an envelope protein of the baculoviridae family. Preferably, the sequence of the heterologous or functionally modified envelope protein of the present invention is derived from the baculoviral envelope protein gp64. Representative gp64 genes and methods of preparing them are known and described, e.g., in Monsma & Blissard, 1995, J. Virol. 69(4):2583–95; Blissard & Rohrmann, 1989, Virology 170(2):537–55; and Blissard & Monsma, U.S. Pat. Nos. 5,750,383 and 5,750,383. For example, a gp64 or other suitable baculovirus envelope genes can be derived from *Autographa californica* nucleopolyhedrovirus (AcMNPV), *Anagrapha falcifera* nuclear polyhedrosis virus, *Bombyx mori* nuclear polyhedrosis virus, *Choristoneura fumiferana* nucleopolyhedrovirus, *Orgyia pseudotsugata* single capsid nuclear polyhedrosis virus, *Epiphyas postvittana* nucleopolyhedrovirus, *Hyphantria cunea* nucleopolyhedrovirus, *Galleria mellonella* nuclear polyhedrosis virus, Dhori virus, Thogoto virus, *Antheraea pernyi* nucleopolyhedrovirus or Batken virus. Preferably, the gp64 envelope gene is an AcMNPV gp64 envelope gene.

However, the heterologous or functionally modified envelope proteins of the present invention are not limited to baculovirus. For example, suitable heterologous or functionally modified envelope proteins can be derived from an envelope protein of a Moloney murine leukemia virus (MoMuLV or MMLV), Harvey murine sarcoma virus (HaMuSV or HSV), murine mammary tumor virus (MuMTV or MMTV), gibbon ape leukemia virus (GaLV or GALV), human immunodeficiency virus (HIV) or Rous sarcoma virus (RSV).

The core sequence of the retroviral vectors of the present invention may be readily derived from a wide variety of retroviruses, including for example, B, C, and D type retroviruses as well as spumaviruses and lentiviruses (see RNA Tumor Viruses, Second Edition, Cold Spring Harbor Laboratory, 1985). An example of a retrovirus suitable for use in the compositions and methods of the present invention includes, but is not limited to, lentivirus. Other retroviruses suitable for use in the compositions and methods of the present invention include, but are not limited to, Avian Leukosis Virus, Bovine Leukemia Virus, Murine Leukemia Virus, Mink-Cell Focus-Inducing Virus, Murine Sarcoma Virus, Reticuloendotheliosis virus and Rous Sarcoma Virus. Particularly preferred Murine Leukemia Viruses include 4070A and 1504A (Hartley and Rowe, J. Virol. 19:19–25, 1976), Abelson (ATCC No. VR-999), Friend (ATCC No. VR-245), Graffi, Gross (ATCC No. VR-590), Kirsten, Harvey Sarcoma Virus and Rauscher (ATCC No. VR-998), and Moloney Murine Leukemia Virus (ATCC No. VR-190). Such retroviruses may be readily obtained from depositories or collections such as the American Type Culture Collection ("ATCC"; Rockville, Md.), or isolated from known sources using commonly available techniques.

Preferably, a retroviral vector sequence of the present invention is derived from a lentivirus. A preferred lentivirus is a human immunodeficiency virus, e.g., type 1 or 2 (i.e., HIV-1 or HIV-2, wherein HIV-1 was formerly called lymphadenopathy associated virus 3 (HTLV-III) and acquired immune deficiency syndrome (AIDS)-related virus (ARV)), or another virus related to HIV-1 or HIV-2 that has been identified and associated with AIDS or AIDS-like disease. Other lentivirus include, a sheep Visna/maedi virus, a feline immunodeficiency virus (FIV), a bovine lentivirus, simian immunodeficiency virus (SIV), an equine infectious anemia virus (EIAV), and a caprine arthritis-encephalitis virus (CAEV).

The various genera and strains of retroviruses suitable for use in the compositions and methods are well known in the art (see, e.g., Fields Virology, Third Edition, edited by B. N. Fields et al., Lippincott-Raven Publishers (1996), see e.g., Chapter 58, Retroviridae: The Viruses and Their Replication, Classification, pages 1768–1771, including Table 1, incorporated herein by reference).

As used herein, a first polynucleotide sequence is "derived from" a second polynucleotide sequence if it has the same or substantially the same base pair sequence as a region of the second polynucleotide sequence, its cDNA, complements thereof, or if it displays sequence identity as described above. Similarly, a first polypeptide sequence is "derived from" a second polypeptide sequence if it is (i) encoded by a first polynucleotide sequence derived from a second polynucleotide sequence, or (ii) displays sequence identity to the second polypeptide sequence as described above.

Two or more polynucleotide sequences can be compared by determining their "percent identity." Two or more amino acid sequences likewise can be compared by determining their "percent identity." The percent identity of two sequences, whether nucleic acid or peptide sequences, is generally described as the number of exact matches between two aligned sequences divided by the length of the shorter sequence and multiplied by 100. An approximate alignment for nucleic acid sequences is provided by the local homology algorithm of Smith and Waterman, Advances in Applied Mathematics 2:482–489 (1981). This algorithm can be extended to use with peptide sequences using the scoring matrix developed by Dayhoff, Atlas of Protein Sequences and Structure, M. O. Dayhoff ed., 5 suppl. 3:353–358, National Biomedical Research Foundation, Washington, D.C., USA, and normalized by Gribskov, Nucl. Acids Res. 14(6):6745–6763 (1986). An implementation of this algorithm for nucleic acid and peptide sequences is provided by the Genetics Computer Group (Madison, Wis.) in their BestFit utility application. The default parameters for this method are described in the Wisconsin Sequence Analysis Package Program Manual, Version 8 (1995) (available from Genetics Computer Group, Madison, Wis.). Other equally suitable programs for calculating the percent identity or similarity between sequences are generally known in the art.

For example, percent identity of a particular nucleotide sequence to a reference sequence can be determined using the homology algorithm of Smith and Waterman with a default scoring table and a gap penalty of six nucleotide positions. Another method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages, the Smith-Waterman algorithm can be employed where default parameters are used for the scoring table (for example, gap open penalty of 12, gap extension penalty of one, and a gap of six). From the data generated, the "Match" value reflects "sequence identity." Other suitable programs for calculating the percent identity or similarity between sequences are generally known in the art, such as the alignment program BLAST, which can also be used with default parameters. Details of these programs can be found at the following internet address: NCBI website.

One of skill in the art can readily determine the proper search parameters to use for a given sequence in the above programs. For example, the search parameters may vary based on the size of the sequence in question. Thus, for example, a representative embodiment of the present invention would include an isolated polynucleotide having X contiguous nucleotides, wherein (i) the X contiguous nucleotides have at least about 50% identity to Y contiguous nucleotides derived from any of the sequences described herein, (ii) X equals Y, and (iii) X is greater than or equal to 6 nucleotides and up to 5000 nucleotides, preferably greater than or equal to 8 nucleotides and up to 5000 nucleotides, more preferably 10–12 nucleotides and up to 5000 nucleotides, and even more preferably 15–20 nucleotides, up to the number of nucleotides present in the full-length sequences described herein (e.g., see the Sequence Listing and claims), including all integer values falling within the above-described ranges.

In preferred embodiments, a retroviral vector sequence of the present invention comprising a CRP gene, packaging gene, transfer gene or heterologous or functionally modified envelope gene is operably linked with at least one regulatory sequence, e.g., a promoter and/or enhancer. The regulatory sequence can be any eukaryotic promoter and/or enhancer, including for example, the Moloney murine leukemia virus promoter-enhancer element, the human cytomegalovirus enhancer or the vaccinia P7.5 promoter. In some cases, such as the Moloney murine leukemia virus promoter-enhancer element, the promoter-enhancer elements are located within or adjacent to the LTR sequences.

Preferably, the regulatory sequence is one which is not endogenous to the lentivirus from which the retroviral vector sequence is derived. For example, if the vector sequence is derived from a lentivirus, the lentiviral regulatory sequence found in the lentivirus LTR can be replaced by a regulatory element which does not originate from the lentivirus.

Preferably, the retroviral vector sequences employed in the retroviral packaging vectors and transfer vectors of the present invention include at least one locus defining element(s), or other elements which control gene expression by other means such as alternate splicing, nuclear RNA export, post-translational modification of messenger, or post-transcriptional modification of protein. Such vector sequences also preferably include a packaging signal, long terminal repeats (LTRs) or portion thereof, and positive and negative strand primer binding sites appropriate to the retrovirus used (if these are not already present in the retroviral vector sequence). Optionally, a retroviral vector sequence of the present invention may include a signal which directs polyadenylation, selectable markers such as Neomycin resistance, TK, hygromycin resistance, phleomycin resistance, histidinol resistance, or DHFR, as well as one or more restriction sites and a translation termination sequence. In some embodiments, the retroviral vector sequences of the present invention include a 5' LTR, a tRNA binding site, a packaging signal, an origin of second strand DNA synthesis, and a 3' LTR or a portion thereof.

Suitable tRNA binding sites and origins of second strand DNA synthesis are known and may be readily identified by one of skill in the art. For example, a retroviral tRNA can bind to a tRNA binding site by Watson-Crick base pairing, and can be carried with the retrovirus genome into a viral particle and utilized as a primer for DNA synthesis by reverse transcriptase. Consequently, a tRNA binding site may be readily identified based on its location just downstream from a 5' LTR. The origin of second strand DNA synthesis is also referred to as the polypurine tract, is located just upstream of the 3' LTR.

In one embodiment, the retroviral vectors of the present invention are self-inactivating (SIN) retroviral vectors. SIN retroviral vectors and methods of making such vectors are known in the are (see e.g., Zufferey et al. (1998) 72:9873–9880; Dull et al. (1998) J. Virol. 72:8463–8471; Xu et al. (2001) Molecular Therapy 3:1–8). Generally, a SIN retroviral vector can be constructed by introducing a deletion or mutation in a retroviral transcriptional regulatory sequence of a retroviral vector to generate a SIN retroviral vector which is replication incompetent and incapable of transcribing a full-length vector RNA in mammalian cells transduced with such vectors.

In a preferred embodiment of the present invention, the retroviral vector of the present invention has a 3'LTR which contains a deletion or mutation that inactivates the transcriptional activity of that 3'LTR ("SIN3'LTR"), thereby, making the vector a SIN retroviral vector. In this embodiment, during the retroviral processing and reverse transcription of the full-length vector RNA, the sequences of the 5'LTR are replaced with the sequences of the SIN3'LTR.

Transcription of a full-length vector RNA can be driven by a promoter in the 5'LTR of a retroviral vector sequence of the present invention. However, the location of the promoter is not limited to the 5'LTR and can be placed in any location where the promoter is operably linked to the respective vector sequence. As used herein "operably linked" refers to an arrangement of elements wherein the components so described are configured so as to perform their usual or intended function. For example, a given promoter operably linked to a gene sequence, or other sequence encoding a protein, is capable of effecting the expression of that sequence. However, the promoter need not be contiguous with the coding sequence, so long as it functions to direct the expression of the operably linked sequence.

The 5' LTR of a retroviral vector sequence of the present invention can be modified by substituting part or all of the transcriptional regulatory elements of the U3 region with heterologous enhancer/promoters. Such changes can be made to enhance the expression of retroviral vector RNA in producer cells and producer cell lines; to allow retroviral vector production in the absence of a HIV tat gene; and to remove an upstream wild-type copy of an HIV LTR that can recombine with the 3' deleted version to "rescue" a SIN retroviral vector. Thus, in some embodiments, the SIN retroviral vector sequences of the present invention have such alterations at the 5' LTR and can be used, e.g., in combination with packaging cells that do not express tat. to generate producer cells or cell lines.

For example, transcription from the HIV LTR is dependent on the transactivator function of the tat protein. In the presence of tat, which can be expressed by a packaging vector, transcription of retroviral vector RNA from the HIV LTR can be strongly stimulated. Where the retroviral vector RNA has a full complement of packaging signals, the RNA is efficiently encapsidated into infectious virions and can be efficiently transferred to target cells. The amount of retroviral vector RNA available for packaging by cells can be a rate-limiting step in the production of recombinant retrovirus carrying a retroviral vector RNA.

The enhancer or the enhancer and promoter regions of a 5' LTR can be substituted, e.g., with the enhancer or the enhancer and promoter of a human cytomegalovirus (CMV) or a murine Rous sarcoma virus (RSV), respectively. The enhancer or the enhancer and promoter regions of a 5' LTR can also be substituted, e.g., with a regulatable promoter such as the tetracycline-inducible promoter.

In a preferred embodiment, a retroviral vector of the present invention has significantly improved biosafety as compared to known retroviral vectors because it has no wild-type copy of the HIV LTR either at the 5' or at the 3' end, and is used in conjunction with tat-less packaging vectors as described herein. Thus, in some preferred embodiments, the present invention provides for packaging vectors wherein the tat sequences are functionally deleted (i.e., the activity and/or function of tat is inactivated). For example, the tat gene can be deleted, in part or in whole, or various point mutations or other mutations can be made to the tat sequence to inactivate the gene.

Where a retroviral vector of the present invention encodes a cytotoxic gene (i.e., a gene that expresses a product deleterious to a host cell), an inducible promoter system is preferably operably linked to the transcription unit of the cytotoxic gene such that the expression of that gene can be regulated to minimize host toxicity when gene expression is not required.

For example, the tetracycline-regulatable gene expression system of Gossen & Bujard (Proc. Natl. Acad. Sci. (1992) 89:5547–5551) can be employed to provide for inducible expression of a gene when tetracycline is withdrawn from the transferred cell. Thus, in one preferred embodiment, the tet/VP16 transactivator is present on a first vector and a coding sequence for a cytotoxic gene is cloned downstream from a promoter controlled by tet operator sequences on another vector.

In addition, a retroviral vector of the present invention can comprise an antigen-binding portion of an antibody or a recombinant antibody-type molecule, such as a single chain antibody, to direct the retroviral vector to a specific cellular target. Those of skill in the art would know of, or could readily ascertain without undue experimentation, specific methods to achieve delivery of a retroviral vector to a specific cellular target.

In preferred embodiments, the methods comprise transforming a host cell with a first nucleotide sequence comprising a gag, a pol, or gag and pol genes; and a second nucleotide sequence comprising a heterologous or functionally modified envelope protein. Preferably, the envelope protein is a baculoviral envelope protein, e.g., gp64. In another preferred embodiment, the retroviral elements are derived from a lentivirus, e.g., HIV. Preferably, the vectors lack a functional tat gene and/or functional accessory genes (vif, vpr, vpu, vpx, nef). In another preferred embodiment, the methods further comprise transforming the host cell with a third nucleotide sequence that comprises a rev gene. Optionally, the method further comprises transforming the host cell with a transfer vector sequence encoding a transgene operably linked to an expression control sequence. The host cell can be cultured under conditions suitable for viral production, and retrovirus carrying transfer vector RNA encoding the transgene can be recovered from the culture medium.

The techniques used to construct vectors, and to transfect and to infect cells, are practiced widely in the art. Practitioners are familiar with the standard resource materials which describe specific conditions and procedures. Construction of the vectors of the present invention employs standard ligation and restriction techniques which are well understood in the art (see Maniatis et al., in Molecular Cloning: A Laboratory Manual, Cold Spring Harbor Laboratory, N.Y., 1982). Isolated plasmids, DNA sequences or synthesized oligonucleotides are cleaved, tailored and religated in the form desired.

Conventional methods can be used to propagate the viruses used in the invention (see, e.g., Burleson, et al., 1992, Virology: A Laboratory Manual, Academic Press, Inc., San Diego, Calif.; and Mahy, ed., 1985, Virology: A Practical Approach, IRL Press, Oxford, UK). Conventional conditions for propagating viruses are suitable for allowing expression of a baculoviral envelope protein on the surface of a retrovirus particle used in the invention.

Methods for the large-scale production of safe and efficient retrovirus packaging lines for use in immunotherapy protocols is described in Farson et al., 1999, J. Gene Medicine 1:195–209. Additional guidance on the production and use of lentiviral vectors is provided in U.S. Pat. No. 6,165,782, issued Dec. 26, 2000, and in PCT Application No. U.S. 00/11097, published Nov. 29, 2000. Transduction efficiency can be enhanced and toxicity minimized or eliminated through the selection of elements for the vector construct as well as through vector purification or concentration. Such methods of purification and of concentration are well known in the art.

Preferred is the use of lentiviral vectors of the present invention that are capable of high infectivity (e.g., more than 20% of target cells expressing transgene, preferably more than 25% of target cells expressing, or an infectivity of at least about $5 \times 10^7$ TU/µg p24 Gag antigen) of quiescent as well as proliferating cells. Also preferred is the use of a purification protocol sufficient to produce a viral stock that is substantially free of non-infectious contaminants. In a preferred embodiment, the lentivirus of the present invention are centrifuged at low speed, filtered, and then concentrated by high speed centrifugation, such as at about 19,500 rpm.

In one embodiment, the retrovirus of the present invention has a titer of $5 \times 10^4$ infectious units/ml. Preferably, retrovirus of the present invention has at least a titer of $1 \times 10^5$, or more preferably, at least $5 \times 10^5$ infectious units/ml, and most preferably, at least $5 \times 10^6$ infectious units/ml. The titer can be determined by known or conventional infectivity assay on a variety of cells, e.g., 293T, HeLa or HUH7 hepatoma cells.

Retroviral-Mediated Gene Transfer

The present invention additionally provides methods for delivering a transgene to a cell, in vivo, in vitro or ex vivo using the retrovirus of the present invention. Also provided are methods of treating a subject and of delivering a therapeutic transgene to cells of a subject using the retrovirus of the present invention. In some embodiments, the transgene is delivered to dividing or quiescent cells in a subject, such as liver cells. The method comprises using the retroviral transfer vectors of the present invention to transduce a cell with a sequence encoding a transgene. Preferably, the transgene is a therapeutic transgene. In preferred embodiments, significant toxicity is not caused in the subject. Toxicity can be minimized or eliminated by use of a vector of the invention, such as those described herein and having an infectivity of at least about $5 \times 10^7$ TU/µg p24$^{Gag}$ antigen.

The retroviral particles of the invention can be administered to a subject parenterally, preferably intravascularly (including intravenously). When administered parenterally, it is preferred that the vector particles of the present invention be given in a pharmaceutical vehicle suitable for injection such as a sterile aqueous solution or dispersion. Following administration, the subject is monitored to detect changes in gene expression. Dose and duration of treatment is determined individually depending on the condition or disease to be treated. A wide variety of conditions or diseases can be treated based on the gene expression produced by administration of the gene of interest in the vector of the present invention.

The dosage of retroviral vector delivered using the methods of the invention will vary depending on the desired response by the host and the vector used. Generally, it is expected that up to 100–200 µg of DNA or RNA can be administered in a single dosage, although a range of 0.5 mg/kg body weight to 50 mg/kg body weight will be suitable for most applications.

Pseudotyping can extend the tissue tropism of the retroviral vectors of the present invention and can increase efficiency of gene transfer into cells. Accordingly, the present invention additionally provides methods of delivering a transgene to a cell using pseudotyped retroviral vectors.

In preferred embodiments, the transgene is a therapeutic transgene. However, the compositions and methods of the present invention can be used to produce any non-retroviral vector sequence, or expression products thereof, in cells specifically for the purpose of reproduction of that sequence (e.g., for cloning) or expression product (e.g., for therapeutic or commercial use). Thus, in one embodiment, the recombinant retrovirus of the present invention act as a cloning vehicle and has utility as such for the reproduction of any transgene sequence that can be packaged into recombinant retrovirus of the present invention for infection and transduction of a cell such that the cell expresses the transgene sequence. In preferred embodiments, the recombinant retrovirus of the present invention can be used for treatment of diseases in a subject where there is defective or deficient expression of gene products, a viral infection, tumor, or cancer.

"Gene transfer" or "gene delivery" as used herein refers to the introduction or delivery of a nucleic acid sequence (e.g., a DNA or RNA sequence) of interest into a host cell (e.g., a target cell, packaging cell, or producer cell) resulting in: 1) the transient expression of non-integrated transferred DNA; 2) extrachromosomal replication and expression of transferred replicons (e.g., episomes); or 3) integration of transferred genetic material into the genomic DNA of host cells.

Retroviral-mediated gene transfer, based upon ex vivo transduction of target cells, is known and, e.g., has been employed in humans. The ability to target delivery and expression of selected genes or nucleic acid sequences into desirable tissue cells in an in vivo setting using retroviral vectors is also known. Thus, retroviral-mediated gene transfer using the compositions of the present invention can be used to effectively treat genetic disorders, tumors and viral infections in a subject. Genetic disorders include, e.g., diseases resulting from lesions in genes. Such diseases may include, for example, hematopoietic and bone marrow disorders, metabolic disorders resulting from defects in liver enzymes and diseases of the central nervous system. Potential clinical applications are thus numerous for such retroviral-mediated gene transfer using the compositions of the present invention.

For some diseases, introduction of a functional homolog of the defective gene and production of even small amounts of the gene product could have a beneficial effect. Other diseases may require a specific amount of gene product to be produced at a specific time, typically in response to a physiological signal (regulated gene expression). An example of such diseases is diabetes, where insulin production requires such regulated gene expression. In such cases gene replacement, rather than gene augmentation which is currently in practice, would be indicated. Otherwise attempts can be made to correct the underlying genetic defect by using genes along with their native regulatory switches (gene augmentation). In other cases, where it is not necessary to correct the genetic lesion in the cell type that exhibits the defect, the gene may be introduced into a different cell type. This is usually true for genes either encoding secretory proteins or enzymes which catalyze the production of secretory products. An example is the case of Parkinson disease where retrovirally transduced fibroblasts encoding tyrosine hydroxylase and capable of making dopamine were intracerebrally implanted in rats. See Wolff, Proc. Natl. Acad. Sci. USA 86:9011–15(1989). However, most genetic diseases require that the defective gene be replaced in the relevant cell type.

Because malignancies appear to result from a number of genetic lesions, both inherited and acquired, which appear to activate oncogenes and/or inactivate tumor suppressor genes, gene therapy applications to treat tumors can take several approaches. One strategy is to enhance the cytotoxic effects of the body's natural defense mechanisms against tumor cells, for example using tumor infiltrating lymphocytes by expressing certain gene products (see e.g., Kasid, Proc. Nat. Acad. Sci. USA 87:473–77(1990); Rosenberg, Cancer Res. Supp. 51:50745–50795(1991); Rosenberg, J. Am. Med. Assn. 268:2614–19(1992); Anderson, Science 256:808–13(1992)). A second approach is directed toward inhibiting the activity of dominantly acting oncogenes (see e.g., Tubiana, Eur. J. Cancer 27:936–39(1991)). Another strategy involves targeted delivery into tumor cells of the genes encoding toxic products or genes conferring sensitivity to toxic drugs, e.g., the thymidine kinase gene of the herpes simplex virus (HSV-TK) (see e.g., Moolten and Wells, J. Natl. Cancer Inst. 82:297–300(1990) and Culver, Science 256:1550–52(1992)). Retroviral vectors transducing HSV-tk gene into tumor cells can enhance the incorporation of nucleoside analogs such as acyclovir and ganciclovir and thereby exhibit tumoricidal effect upon administration of these drugs.

Gene therapy also finds utility in the treatment of virally induced conditions, such as HIV and HTLV-I infections. The regulatory proteins or response elements of HIV and HTLV-I necessary for virus production are potential targets. Mutants of these proteins could be introduced to compete with the native viral proteins. In addition, antisense RNAs complementary to retroviral RNAs are being employed to specifically inhibit replication of HIV and HTLV-I (see e.g., Rhodes and James, AIDS 5:145–51(1991); von Rueden and Gilboa, J. Virol. 63:677–82(1989)). Retroviral vectors carrying HIV-specific antisense sequences or ribozymes could be used to inhibit expression of HIV for cellular immunization. Triple stranded RNA complexes, in which double-stranded RNA is locked into conformation by a third strand could prove an effective way of silencing viral gene expression by designing retroviral vectors encoding an antisense and an anti parallel triple stranded RNA on a single molecule from a retroviral vector (see, e.g., Giovannangeli, J. Am. Chem. Soc. 113:7775–77(1991).

In general, retroviral vectors offer advantages over other viral gene transfer vehicles and other gene transfer methods including, for mammalian systems, electroporation, $CaPO_4$ precipitation, DEAE-dextran, direct DNA injection and lipofection. Retroviruses carry genetic information in the RNA form, reverse transcribing a DNA form upon infection that efficiently integrates into the genomic DNA of the infected cell and, thereby, offer stable propagation of the integrated sequence in the progeny cells of the transduced parent cell. Retroviral integration is site-specific with respect to viral ends, and the provirus is usually intact and colinear with the viral genome, i.e., the LTR-gag-pol-env-LTR gene order is maintained by the provirus which, consequently, reduces the possibility of DNA rearrangements and/or deletions, as is commonly observed with random pathway integration. Cells infected with replication defective retroviral vectors do not express viral proteins and thus are not susceptible to immune clearance. In addition, the efficiency of gene transfer and stable expression in transduced cells can be very high with such vectors. For these reasons such retroviral vectors have been approved for use in human gene therapy.

While ex vivo therapeutic regimens have found success in treating certain genetic disorders, other disorders need to be treated using an in vivo therapeutic approach because the genetic disorder affect cell types not easily isolated. Thus, preferably, the packaged retroviral vector is not inactivated by specific host humoral or cellular immune responses or by non-specific responses such as complement or other blood factors. In such applications, it is also preferable that the retroviral vector infects only the cells in which the defect manifests itself. In a preferred embodiment, the expression of the therapeutic gene is controlled by regulatory elements that target expression to the relevant cell type.

Retroviruses can be classified according to their host range. For example, ecotropic murine retroviruses such as MuLV (MuLV-E) infect only murine cells. Xenotropic murine retroviruses such as MuLVs (MuLV-X) infect non-murine cells. Amphotropic murine retroviruses such as MuLVs (MuLV-A) infect both murine and non-murine cells, including human cells. As described herein, the host range and cell tropism is determined primarily by the viral envelope protein and the availability of specific receptor proteins on the host cells. Thus, using the compositions and methods of the present invention, the host range of a retrovirus can be altered by pseudotyping.

Other approaches to modifying the tissue-infecting capacity of retroviral vectors to achieve viral targeting involve the use of bivalent, streptavidin-linked antibodies. Other approaches involve generating functionally modified envelope proteins by fusion or chemical coupling of ligands or proteins that bind to specific cellular targets to an envelope protein. For example, one approach involves the fusion or chemical coupling of a ligand (e.g., a receptor or antibody) to an envelope protein. For example, by coupling the envelope protein to lactose, the protein becomes an artificial asialoglycoprotein which is internalized by specific receptors on hepatocyte cells (see e.g., Neda, J. Biol. Chem. 226:14143–46(1991)). An additional approach involves mutation of the receptor recognition region of the envelope gene to generate chimeric envelope proteins. For example, an engineered MoMuLV-E vector bearing a chimeric erythropoietin-envelope (EPO-envelope) protein on its surface has exhibited infectivity for cells that bear the EPO receptor, both of murine and human origin (see e.g., Kasahara, Science 266:1373–76(1994)). This chimeric construct has an EPO encoding sequence substituted for the N-terminal region of the envelope gene, and, although the chimeric MoMuLV-E construct exhibits tissue targeting, it requires complementation from the wild type envelope protein.

Transgene Sequences

The retroviral transfer vector sequences of the present invention can encode one or more transgene sequences (i.e., a gene or gene fragment, or more than one gene or gene fragment or other sequence encoding a protein). Any of the polynucleotide sequences described herein may be used to identify fragments or full-length coding sequences of the genes to which they are associated and may be suitable for use in the compositions and methods of the present invention. Methods of isolating fragments or full-length sequences of genes are well known in the art.

Such genes and/or gene fragments can comprise any sequence useful in gene therapy or for any other purpose (e.g., cloning or product production). See e.g. WO96/21014 and WO91/02805 for a description of nucleic acid sequences of therapeutic interest that can be introduced into the retroviral vectors of the invention. Preferably, the transgene sequence encodes a protein, e.g., a hormone, enzyme, receptor, or single chain antibody useful in gene therapy.

The transgene sequence can be any nucleic acid sequence of interest which can be transcribed. Generally, the transgene sequence encodes a polypeptide. Preferably, the polypeptide has some therapeutic benefit. For example, the polypeptide may supplement deficient or nonexistent expression of an endogenous protein in a host cell. The polypeptide can confer new properties on the host cell, such as a chimeric signaling receptor, see e.g., U.S. Pat. No. 5,359,046. The artisan can determine the appropriateness of a transgene sequence practicing techniques taught herein and known in the art. For example, the artisan would know whether a transgene sequence is of a suitable size for encapsidation and whether the transgene sequence product is expressed properly.

Preferably, a transgene sequence encoded by a retroviral vector sequence of the present invention is operably linked to a promoter that is internal to the transcription regulatory sequences of the retroviral vector sequence. "Operably linked" as used herein with reference to a transgene sequence refers to a functional linkage between a regulatory sequence and a transgene nucleic acid sequence resulting in expression of the transgene sequence in cells.

It may be desirable to modulate the expression of a gene regulating molecule in a cell by the introduction of a molecule using the compositions and methods of the invention. The term "modulate" envisions the suppression of expression of a gene when it is over-expressed or augmentation of expression when it is under-expressed. Where a cell proliferative disorder is associated with the expression of a gene, nucleic acid sequences that interfere with the expression of a gene at the translational level can be used. The approach can utilize, for example, antisense nucleic acid, ribozymes or triplex agents to block transcription or translation of a specific mRNA, either by masking that RNA with an antisense nucleic acid or triplex agent, or by cleaving same with a ribozyme.

Antisense nucleic acids are DNA or RNA molecules which are complementary to at least a portion of a specific mRNA molecule (Weintraub, Sci. Am. (1990) 262:40). In the cell, the antisense nucleic acids hybridize to the corresponding mRNA forming a double-stranded molecule. The antisense nucleic acids interfere with the translation of the mRNA since the cell will not translate a mRNA that is double-stranded. Antisense oligomers of about 15 nucleotides or more are preferred since such are synthesized easily and are less likely to cause problems than larger molecules when introduced into the target cell. The use of antisense methods to inhibit the in vitro translation of genes is well known in the art (see e.g., Marcus-Sakura, Anal. Biochem. (1988) 172:289).

Useful antisense nucleic acids also include small-interfering RNA (siRNA) molecules. Methods of using siRNA to inhibit gene expression are well known in the art (see e.g., U.S. Pat. No. 6,506,559).

The antisense nucleic acid can be used to block expression of a mutant protein or a dominantly active gene product, such as amyloid precursor protein that accumulates in Alzheimer's disease. Such methods are also useful for the treatment of Huntington's disease, hereditary Parkinson's and other diseases. Antisense nucleic acids are also useful for the inhibition of expression of proteins associated with toxicity.

Use of an oligonucleotide to stall transcription can be by the mechanism known as the triplex strategy since the oligomer winds around double-helical DNA, forming a three-strand helix. Therefore, the triplex compounds can be designed to recognize a unique site on a chosen gene (see e.g., Maher et al., Antisense Res. and Dev. (1991) 1(3):227; Helene, Anticancer Drug Dis. (1991) 6(6):569).

Ribozymes are RNA molecules possessing the ability to specifically cleave other single-stranded RNA in a manner analogous to DNA restriction endonucleases. Through the modification of nucleotide sequences which encode those RNA's, it is possible to engineer molecules that recognize and cleave specific nucleotide sequences in an RNA molecule (see e.g., Cech, J. Amer. Med Assn. (1988) 260:3030). A major advantage of that approach is only mRNA's with particular sequences are inactivated.

The desired transgene sequence or sequences are preferably non-retroviral sequences that are inserted into a retroviral transfer vector sequence of the present invention. However, in some cases a desired therapeutic gene may be a retroviral gene, e.g., a sequence encoding an HIV structural protein capable of inducing an anti-HIV immune response. Such therapeutic retroviral sequences are preferably recombinant or heterologous with respect to the retroviral vector sequence (e.g., an HIV-1 therapeutic gene sequence is inserted into a MuLV vector sequence of the present invention).

For example, to enhance the body's natural cytotoxic defense mechanisms, recombinant retroviral vectors of the invention may include sequences which stimulate the production of, or genetically modify, tumor infiltrating lymphocytes (TIL). TIL transduced ex vivo with a retroviral vector expressing neo gene have been employed to study their homing sites in the human hosts. Similarly, TIL transduced with tumor necrosis factor (TNF) have been used to treat human subjects with advanced melanoma. In addition, TIL transduced with chimeric T cell receptor (TcR) consisting of the constant region of the TcR and the variable region of a monoclonal antibody can be redirected to lyse cancer cells recognized by the monoclonal antibody.

The nucleic acid sequence inserted into the retroviral vector can be, e.g., a viral structural gene that is capable of inducing an immune response against a viral infection in a subject. Additionally, the nucleic acid sequence inserted into the retroviral vector can be, e.g., any other gene useful for vaccination or immunization of a subject (e.g., a bacteria or protozoa, particularly a pathogen, or a gene encoding a tumor antigen). In the particular case of disease caused by HIV infection, where immunostimulation is desired, the antigen generated from a recombinant retrovirus may be in a form which will elicit either or both an HLA class I- or class II-restricted immune response. In the case of HIV envelope antigen, for example, the antigen is preferably selected from gp 160, gp 120, and gp 41, which have been modified to reduce their pathogenicity. In particular, the selected antigen is modified to reduce the possibility of syncytia, to avoid expression of epitopes leading to a disease enhancing immune response, to remove immunodominant, but haplotype-specific epitopes or to present several haplotype-specific epitopes, and allow a response capable of eliminating cells infected with most or all strains of HIV.

The haplotype-specific epitopes can be further selected to promote the stimulation of an immune response within an animal which is cross-reactive against other strains of HIV. Antigens from other HIV genes or combinations of genes, such as gag, pol, rev, vif, nef, prot, gag/pol, gag prot, etc., may also provide protection in particular cases. HIV is only one example. This approach should be effective against many virally linked diseases or cancers where a characteristic antigen (which does not need to be a membrane protein) is expressed, such as in HPV and cervical carcinoma, HTLV-I-induced leukemias, prostate-specific antigen (PSA) and prostate cancer, mutated p53 and colon carcinoma and melanoma, melanoma specific antigens (MAGEs), and melanoma, mucin and breast cancer.

A variety of cytokine or immunomodulatory genes may be inserted into the retroviral vectors of the invention. Representative examples of immunomodulatory factors include cytokines, such as IL-1, IL-2 (see e.g., Karupiah et al., J. Immunology 144:290–298, 1990; Weber et a., J. Exp. Med. 166:1716–1733, 1987; Gansbacher et al., J. Exp. Med. 172:1217–1224, 1990; U.S. Pat. No. 4,738,927), IL-3, IL-4 (see e.g., Tepper et al., Cell 57:503–512, 1989; Golumbek et al., Science 254:713–716, 1991; U.S. Pat. No. 5,017,691), IL-5, IL-6 (see e.g., Brakenhof et al., J. Immunol. 139:4116–4121, 1987; WO 90/06370), IL-7 (see e.g., U.S. Pat. No. 4,965,195), IL-8, IL-9, IL-10, IL-11, IL-12, IL-13 (see e.g., Cytokine Bulletin, Summer 1994), IL-14 and IL-15, particularly IL-2, IL-4, IL-6, IL-12, and IL-13, alpha interferon (see e.g., Finter et al., Drugs 42(5):749–765, 1991; U.S. Pat. No. 4,892,743; U.S. Pat. No. 4,966,843; WO 85/02862; Nagata et al., Nature 284:316–320, 1980; Familletti et al., Methods in Enz. 78:387–394, 1981; Twu et al., Proc. Natl. Acad. Sci. USA 86:2046–2050,1989; Faktor et al., Oncogene 5:867–872, 1990), beta interferon (see e.g., Seif et al., J. Virol. 65:664–671, 1991), gamma interferons (see e.g., Radford et al., The American Society of Hepatology 2008-2015, 1991; Watanabe et al., PNAS 86:9456–9460, 1989; Gansbacher et al., Cancer Research 50:7820–7825, 1990; Maio et al., Can. Immunol. Immunother. 30:34–42, 1989; U.S. Pat. No. 4,762,791; U.S. Pat. No. 4,727,138), G-CSF (see e.g., U.S. Pat. Nos. 4,999,291 and 4,810,643), GM-CSF (WO 85/04188), tumor necrosis factors (TNFs) (see e.g., Jayaraman et al., J. Immunology 144:942–951, 1990), CD3 (see e.g., Krissanen et al., Immunogenetics 26:258–266, 1987), ICAM-1 (see e.g., Altman et al., Nature 338:512–514, 1989; Simmons et al., Nature 331:624–627, 1988), ICAM-2, LFA-1, LFA-3 (see e.g., Wallner et al., J. Exp. Med. 166(4):923–932, 1987), MHC class I molecules, MHC class II molecules, B7.1-3, b.sub.2-microglobulin (see e.g., Parnes et al., PNAS 78:2253–2257, 1981), chaperones such as calnexin, MHC linked transporter proteins or analogs thereof (see e.g., Powis et al., Nature 354:528–531, 1991). Immunomodulatory factors may also be agonists, antagonists, or ligands for these molecules. For example soluble forms of receptors can often behave as antagonists for these types of factors, as can mutated forms of the factors themselves.

Within one embodiment, the gene encodes gamma-interferon. Immunomodulatory factors may also be agonists, antagonists, or ligands for these molecules. For example soluble forms of receptors can often behave as antagonists for these types of factors, as can mutated forms of the factors themselves. Genes encoding any of the cytokine and immunomodulatory proteins described herein can be expressed in a retroviral vector to achieve long term in vivo expression. Other forms of these cytokines which are know to those of skill in the art can also be used. For instance, nucleic acid sequences encoding native IL-2 and gamma-interferon can be obtained as described in U.S. Pat. Nos. 4,738,927 and 5,326,859, respectively, while useful muteins of these proteins can be obtained as described in U.S. Pat. No. 4,853,332. As an additional example, nucleic acid sequences encoding the short and long forms of mCSF can be obtained as described in U.S. Pat. Nos. 4,847,201 and 4,879,227, respectively. Retroviral vectors expressing cytokine or immunomodulatory genes can be produced as described herein and in PCT publication number U.S. Ser. No. 94/02951 entitled "Compositions and Methods for Cancer Immunotherapy".

A variety of different forms of IGF-1 and IGF-2 growth factor polypeptides are also well known the art and can be incorporated into retroviral vectors for long term expression in vivo. See e.g. European Pat. No. 0123228B1, grant published on Sep. 19, 1993, entitled "Hybrid DNA Synthesis of Mature Insulin-like Growth Factors". As an additional example, the long term in vivo expression of different forms of fibroblast growth factor can also be effected by the methods of invention. See, e.g. U.S. Pat. No. 5,464,774, issued Nov. 7, 1995, U.S. Pat. No. 5,155,214, and U.S. Pat. No. 4,994,559, for a description of different fibroblast growth factors.

As additional examples, Factor VII or Factor IX is useful for treatment of blood clotting disorders, such as hemophilia. Different forms of Factor VII, such as the B domain deleted Factor VII construct described in WO 96/21014 can be used to produce retroviral vectors expressing Factor VII for use in the methods of the invention. In addition to clotting factors, there are a number of proteins which can be expressed in the retroviral vectors of the invention and which are useful for treatment of hereditary diseases. These include lactase for treatment of hereditary lactose intolerance, AD for treatment of ADA deficiency, and alpha-1 antitypsin for treatment of alpha-1 antitrypsin deficiency (see e.g., F. D. Ledley, J. Pediatics, 110, 157–174 (1987); I. Verma, Scientific American (November, 1987) pp. 68–84; and PCT Publication WO 9527512 entitled "Gene Therapy Treatment for a Variety of Diseases and Disorders" for a description of gene therapy treatment of genetic diseases).

Alternatively, the recombinant retroviral vectors of the invention may include inducible genes encoding toxic products or genes which confer sensitivity to a toxic drug (suicidal vector approach). An example of a gene encoding a toxic product is the diphtheria toxin gene. An example of a gene that confers sensitivity to a toxic drug is the herpes simplex virus TK gene, which enhances the capacity of cells to metabolize and incorporate nucleoside analogs such as acyclovir and ganciclovir. A variety of other prodrug converting enzymes can also be used in the retroviral vectors of the invention (see, e.g., WO 95/14091 and EP 0 415 731 for a description of viral thymidine kinase and other prodrug converting systems for use in the retroviral vectors of the invention).

The recombinant retroviral vectors of the invention may include sequences, genes and/or gene fragments that encode either wild type or mutant forms of HIV or HTLV-I regulatory proteins or response elements that are required for virus production (e.g., gag and rev proteins and TAR sequence of HIV). These sequences may be modified by the addition, substitution, or deletion of nucleotides to change the reading frame of the protein or by N- or C-terminal truncation or deletion of an internal sequence of nucleotides to result in the expression of a trans dominant or competing defective HIV or HTLV-I protein or response element. Delivery of the recombinant retroviral vectors of the invention carrying these wild type, defective or trans dominant-acting mutant sequences would "arm" the transduced cells with "decoy" proteins to either directly inhibit the replication of the infecting virus or to cause replication incompetency and abortive infection by the packaged virion particles.

Alternatively, the recombinant retroviral vectors of the invention may include sequences coding for antisense RNA or ribozyme against HIV or HTLV-I that specifically inhibit virus replication and would therefore find use in therapeutic and probably the prophylactic treatments for HIV or HTLV-I infection.

The retroviral transfer vectors of the present invention may include sequences, genes and/or gene fragments to treat genetic diseases resulting from the expression of defective gene product/s such as severe combined immunodeficiency, chronic granulomatosis, Gaucher disease, sickle cell anemia, α- and β-thalasemias, Lesch-Nyhan syndrome, duchenne muscular distrophy, parkinson disease, emphysema, cystic fibrosis, phenylketonuria, familial hypercholesterolemia or hemophilia A and B. Such diseases are characterized by a deficiency of a specific gene product which affects a specific cell type.

For example, chronic granulomatosis is characterized by a deficiency in the cytochrome b which affects neutrophils; duchenne muscular dystrophy is characterized by a deficiency in the dystrophin which affects muscle cells; familial hypercholesterolemia is characterized by a deficiency in low-density lipoprotein which affects hepatocytes; gaucher disease is characterized by a deficiency in glucocerebrosidase which affects macrophages; hemophilia A and B is characterized by a deficiency in Factors VIII and IX which affects endothelial cells; lesch-nyhan hypoxanthine syndrome is characterized by a deficiency in phosphoribosyl transferase which affects basal ganglia; parkinson disease is characterized by a deficiency in dopamine which affects substantia nigra; phenylketonuria is characterized by a deficiency in phenylalamine hydroxylase which affects hepatocytes; severe combined immunodeficiency is characterized adenosine deaminase which affects T and B lymphocytes; sickle cell anemia is characterized by a deficiency in β-globin which affects erythrocytes; and α- and β-thalassemias are characterized by a deficiency in α- and β-globin which affects erythrocytes.

Within the recombinant retroviral vectors of the invention, the desired sequences, genes and/or gene fragments can be inserted at several sites (e.g., at a restriction enzyme site or polylinker) and operably linked to different regulatory sequences. For example, a site for insertion can be the viral enhancer/promoter proximal site (i.e., 5'LTR-driven gene locus). Alternatively, the desired sequences can be inserted into the viral promoter distal site, where the expression of the desired sequence or sequences is through splicing of the promoter proximal cistron, an internal heterologous promoter as SV40 or CMV, or an internal ribosome entry site (IRES).

The retroviral vectors of the invention may additionally include a marker sequence(s) or marker gene(s) which encode(s) a protein conferring antibiotic resistance or which provide a molecular tag on transduced cells to permit their isolation by positive selection or by cell sorting devices. Examples of antibiotic resistance include the aminoglycoside phosphotransferase gene which is encoded by neo (aph) and confers resistance to neomycin or G418 (see e.g., Southern, J. Mol. Appl. Gen. 1:327(1982)), and the hygromycin-B-phosphotransferase gene which is encoded by hyg (hph) and confers resistance to hygromycin-B (see e.g., Gritz, Gene 25:179(1983); Sugden, Mol. Cell. Biol. 5:410(1985); Palmer, Proc. Natl. Acad. Sci. USA 84:1055 (1987)). Exemplary molecular tags include chimeric or wild type CD8 proteins and the nucleotide sequences encoding such proteins.

Nucleic acid molecules that encode the above-described substances, as well as other nucleic acid molecules that are advantageous for use within the present invention, may be readily obtained from a variety of sources, including for example depositories such as the American Type Culture Collection (ATCC, Rockville, Md.), or from commercial sources such as British BioTechnology Limited (Cowley, Oxford England). Representative examples include BBG 12 (containing the GM-CSF gene coding for the mature protein of 127 amino acids), BBG 6 (which contains sequences encoding gamma interferon), ATCC No. 39656 (which contains sequences encoding TNF), ATCC No. 20663 (which contains sequences encoding alpha interferon), ATCC Nos. 31902, 31902 and 39517 (which contains sequences encoding beta interferon), ATCC No. 67024 (which contains a sequence which encodes Interleukin-1b), ATCC Nos. 39405, 39452, 39516, 39626 and 39673 (which contains sequences encoding Interleukin-2), ATCC Nos. 59399, 59398, and 67326 (which contain sequences encoding Interleukin-3), ATCC No. 57592 (which contains sequences encoding Interleukin-4), ATCC Nos. 59394 and 59395 (which contain sequences encoding Interleukin-5), and ATCC No. 67153 (which contains sequences encoding Interleukin-6).

Alternatively, cDNA sequences for use with the present invention may be obtained from cells which express or contain the sequences. Briefly, within one embodiment mRNA from a cell which expresses the gene of interest is reverse transcribed with reverse transcriptase using oligo dT or random primers. The single stranded cDNA may then be amplified by PCR (see e.g., U.S. Pat. Nos. 4,683,202, 4,683,195 and 4,800,159; PCR Technology: Principles and Applications for DNA Amplification, Erlich (ed.), Stockton Press, 1989)) utilizing oligonucleotide primers complementary to sequences on either side of desired sequences. In particular, a double stranded DNA is denatured by heating in the presence of heat stable Taq polymerase, sequence specific DNA primers, ATP, CTP, GTP and TTP. Double-stranded DNA is produced when synthesis is complete. T his cycle may be repeated many times, resulting in a factorial amplification of the desired DNA. Nucleic acid molecules which are carried and/or expressed by the recombinant retroviruses described herein may also be synthesized, for example, on an Applied Biosystems Inc. DNA synthesizer (e.g., APB DNA synthesizer model 392 (Foster City, Calif.).

The following examples are presented to illustrate the present invention and to assist one of ordinary skill in making and using the same. The examples are not intended in any way to limit the scope of the invention.

EXAMPLES

The results of the experiments described in the following examples demonstrate that lentivirus-producing cells can be modified to express DAF/CD55, and that producer cells so modified can produce viral particles that are resistant to inactivation by the complement arm of human serum. This method produces recombinant lentiviral particles to very high titer, providing a gene delivery system that offers the advantages of retroviral and lentiviral vectors without the disadvantage of inactivation by complement. Protection of lentivector particles from complement inactivation offers a critical advantage for successful gene therapy applications, particularly those involving intravenous administration of vector.

Example 1

Preparation of Recombinant 3rd Generation Lentiviral Vectors Incorporating the DAF Complement Inhibitor Protein A commercial source of DNA was used to isolate the gene for DAF/CD55. The DAF sequence was PCR amplified from plasmid DNA purchased commercially from the American Type Culture Collection (ATCC). This product is known as Human I.M.A.G.E. Consortium Clone No. 3317033, and the clone was deposited with the ATCC and assigned Accession No. 5530612. A DAF expression plasmid was constructed and used in the preparation of recombinant lentiviral vectors. The lentiviral vector into which DAF was incorporated was tested in a complement inactivation assay. In the absence of DAF/CD55, the infectivity of lentiviral vectors is reduced up to 1000-fold after exposure to human serum. Incorporation of DAF/CD55 into the lentivector particles confers almost 100% protection from this inactivation.

The present examples employ third-generation HIV lentiviral vectors (see e.g., Kumar et al., Hum. Gene Ther. (2003) 14:67–77). The HIV vectors employed in these examples have three HIV genes deleted (tat, nef and vpu) and the vectors are produced through expression of Rev protein in trans (see e.g., Dull et al., (1998) J. Virol., 72:8463–8471).

Example 2

Production of Recombinant 3rd Generation Lentiviral Vectors Incorporating the DAF Complement Inhibitor The recombinant third-generation lentiviral vectors described above were produced by transient transfection into 293T cells as follows: $5\times10^6$ 293T cells were seeded in 10-cm diameter dishes 24 hours prior to transfection in Iscove's Modified Dulbecco's Medium (JRH Biosciences) with 10% heat-inactivated, irradiated Fetal Bovine Serum (JRH Biosciences), penicillin (100 IU/ml)/streptomycin (100 $\mu$g/ml, Gibco) and 2 mM L-glutamine (JRH Biosciences) in a 5% CO2 incubator. The culture medium was changed 2 hours prior to transfection. Plasmid DNA as follows was used to transfect 1 dish: 3.5 $\mu$g of VSV-G envelope plasmid pMD2-VSVG-env; 6.5 $\mu$g of packaging plasmid pMDLg/pRRE; 2.5 $\mu$g of Rev plasmid pRSV-Rev; and 10 $\mu$g of transfer vector plasmid pRRLsinCMVGFPpre. For preps incorporating the DAF protein, a fifth plasmid was included in the transfection: 10 $\mu$g of pMD2-DAF, a DAF expression plasmid. The precipitate was formed using calcium-phosphate precipitation with reagents and procedures obtained from Clontech (CalPhos Transfection Kit, #K2051-1). Medium was replaced 16 hours after transfection. Conditioned medium was collected after another 24 hours, filtered through a 0.22 $\mu$m cellulose acetate filter and concentrated by ultracentrifugation in a SW28 Rotor at 19,500 rpm for 2 h 20 min (concentrated).

Titers were determined by infecting 293T cells in a 6-well plate format: $5\times10^4$ cells per well were seeded 24 hours prior to infection. Vector-containing medium was serially diluted 10-fold in culture medium and 1 ml of diluted vector was used to infect 1 well of target cells in the presence of Polybrene (8 μg/ml) in 2 ml total volume. Medium on the infected cells was changed 24 hours later. After another 48 hours, transduced cells were harvested by trypsinization and resuspension in 1 ml medium. Cells were pelleted by centrifugation in a clinical centrifuge for 2 min and resuspended in fixing medium: PBS+1% Formaldehyde (Sigma). Cells were stored at 4° C. until FACS analysis for % GFP-positive cells using a Becton-Dickinson FACSort. Titer is calculated with the following formula: %GFP positive cells/100×cell number ($1\times10^5$ for 293T)×dilution factor=infectious units/ml. (Only percentages less than 25% were used because FACS analysis is not linear over 25%.)

Example 3

Production of Recombinant 3rd Generation Lentiviral Vectors Incorporating the DAF Complement Inhibitor Protein and Testing for Human Serum Complement Sensitivity Complement sensitivity was determined using the following procedure. Serum from individual human donors was split into two portions and one portion of each was heat-inactivated at 56° C. for 1 hour to eliminate complement activity. Two concentrated vector preps were diluted to a total of $1\times10^6$ infectious units/ml: 1 prep of VSVG-pseudotyped $3^{rd}$ generation lentiviral vector (No DAF) and 1 prep of VSVG-pseudotyped $3^{rd}$ generation lentiviral vector with DAF protein incorporated. The vector preps were diluted 1:4 into normal or heat-inactivated human serum and incubated at 37° C. for 1 hour. Control reactions were carried out with vector diluted 1:4 into medium (No Serum). Each reaction was diluted another 5-fold with medium and two more 10-fold serial dilutions were made from each sample. The three dilutions for each reaction were used to infect 293T cells in a titer assay as outlined above. Medium on the infected cells was changed 24 hours later. After another 72 hours the infected cells were collected by trypsinization and suspended in PBS/1% Formaldehyde. % GFP-positive cells was determined by FACS analysis and titer values were calculated for each reaction. The titer determined for the control reaction (vector incubated in the absence of serum) was set as the arbitrary 100% titer recovery for that vector prep. Titers determined for vector incubated in presence of normal or heat-inactivated serum were compared to the control value and reported as relative percentage recovery.

The results of the above experiments are described as follows and illustrated in FIGS. 1–3.

FIG. 1 shows that DAF confers complement resistance to VSVG-pseudotyped lentiviral vectors. This figure shows the relative recovery of titer after exposure to serum containing (normal serum) or lacking (heat-inactivated serum) complement activity. Presented in FIG. 1 are composite results from two independent experiments with two independent sets of vector preparations. The data on the left side of FIG. 1 show that lentiviral vectors pseudotyped with VSVG envelope protein are sensitive to inactivation by complement in serum from a subset of human donors. Comparing the white bars (complement-active) to the black bars (complement-inactive) shows that the vectors can lose from 3 to 50-fold infectious units. Most donors show at least 10-fold inactivation of the vector. As shown on the right side of FIG. 1, vectors incorporating DAF incubated with serum from the same human donors show very little complement-dependent inactivation. The incorporation of DAF protects the vector from inactivation up to 100% with residual inactivation at less that 4-fold.

FIG. 2 shows that MCP/CD46 can also protect VSV-G pseudotyped lentiviral vectors from human complement inactivation. Lentiviral vectors with and without complement inhibitor proteins were tested for sensitivity to complement inactivation as in FIG. 1. The vector samples tested carried the GFP transgene and were pseudotyped with the VSV-G envelope glycoprotein. One preparation (VSVG, left) was made in absence of any exogenous complement inhibitor protein and the others (VSVG+DAF, middle) and (VSVG+MCP) were generated by co-transfection of mammalian expression plasmids encoding DAF/CD55 or MCP/CD46, respectively. The serum samples were from five single human donors.

FIG. 3 shows that DAF/CD55 also protects gp64-pseudotyped vector from complement inactivation. Lentiviral vectors with and without complement inhibitor proteins were tested for sensitivity to complement inactivation as in FIG. 1. The vector samples tested carried the GFP transgene and were pseudotyped with the baculovirus gp64 envelope glycoprotein. One preparation (gp64, left) was made in absence of any exogenous complement inhibitor protein and the other (gp64+DAF, right) was generated by co-transfection of a mammalian expression plasmid encoding DAF/CD55. The serum samples were from five single human donors.

What is claimed is:

1. A lentivirus packaging cell comprising:

(a) a first nucleotide sequence comprising a gag, a pol, or gag and pol genes;

(b) a second nucleotide sequence comprising a heterologous envelope gene; and (c) a third nucleotide sequence that encodes a complement regulatory protein (CRP) that is not fused to a transmembrane region of an envelope protein.

2. The packaging cell of claim 1, wherein the CRP comprises decay accelerating factor (DAF).

3. The packaging cell of claim 1, wherein the CRP comprises CD59, membrane cofactor protein (MCP), complement receptor 1 (CR1) homologous restriction factor (HRF).

4. The packaging cell of claim 1, wherein the first, second and third nucleotide sequences are stably integrated into the genome of the packaging cell.

5. The packaging cell of claim 1, wherein the lentivirus is a human immunodeficiency virus (HIV).

6. The packaging cell of claim 5, wherein the HIV is HIV-1.

7. The packaging cell of claim 1, which lacks a functional rat gene.

8. The packaging cell of claim 1, further comprising a fourth nucleotide sequence that comprises a rev gene.

9. The packaging cell of claim 1, which lacks functional genes selected from vif, vpr, vpu, vpx and nef, or a combination thereof.

10. The packaging cell of claim 1, wherein the envelope gene comprises a VSV-G envelope gene.

11. A lentiviral producer cell comprising the packaging cell of claim 1 and a lentiviral transfer vector.

12. The lentiviral producer cell of claim 11, which has a titer of at least about $5\times10^5$ infectious units per ml.

13. The lentiviral producer cell of claim 11, which has a titer of at least about $2\times10^6$ infectious units per ml.

14. The lentiviral producer cell of claim 11, which has a titer of at least about $1 \times 10^7$ infectious units per ml.

15. A set of lentiviral vectors comprising:
   (a) a first nucleotide sequence comprising a gag, a pol, or gag and pol genes operably linked to an expression control sequence;
   (b) a second nucleotide sequence comprising a heterologous envelope gene operably linked to an expression control sequence; and
   (c) a third nucleotide sequence that encodes a complement regulatory protein (CRP) operably linked to an expression control sequence, wherein the CRP is not fused to a transmembrane region of an envelope protein.

16. The set of claim 15, wherein the CRP comprises decay accelerating factor (DAF).

17. The set of claim 15, wherein the CRP comprises CD59, MCP, CR1 or HRF.

18. The set of claim 15, wherein the second nucleotide sequence and the third nucleotide sequence are provided on a single construct.

19. A method of producing a lentiviral packaging cell comprising transforming a cell with the set of vectors of claim 15.

20. A method of producing a lentiviral producer cell comprising transforming a packaging cell of claim 1 with a lentiviral transfer vector.

21. A method of producing a recombinant lentivirus comprising culturing a producer cell of claim 11 in a medium and recovering recombinant lentivirus from the medium.

22. A method of delivering a transgene to a cell comprising contacting the cell with a recombinant lentivirus produced by the producer cell of claim 11 under conditions permitting transformation of the cell.

* * * * *

UNITED STATES PATENT AND TRADEMARK OFFICE
CERTIFICATE OF CORRECTION

PATENT NO. : 6,790,641 B2
DATED : September 14, 2004
INVENTOR(S) : Schauber et al.

Page 1 of 1

It is certified that error appears in the above-identified patent and that said Letters Patent is hereby corrected as shown below:

<u>Column 26,</u>
Line 53, "rat" should read -- tat --

Signed and Sealed this

Nineteenth Day of April, 2005

JON W. DUDAS
*Director of the United States Patent and Trademark Office*